United States Patent [19]

Schiltz et al.

[11] Patent Number: 4,965,450

[45] Date of Patent: Oct. 23, 1990

[54] RADIOACTIVE ASSAY FOR MEASURING WATER ABSORPTION BY HUMECTANTS

[75] Inventors: John R. Schiltz, Ramsey; Wanda Nabial, Somerville, both of N.J.

[73] Assignee: American Cyanamid Company, Stamford, Conn.

[21] Appl. No.: 276,821

[22] Filed: Nov. 28, 1988

Related U.S. Application Data

[63] Continuation-in-part of Ser. No. 815,484, Jan. 2, 1986, abandoned.

[51] Int. Cl.$^5$ .................. G01N 37/00; G21H 5/02
[52] U.S. Cl. .................................. 250/303; 436/56; 73/73; 73/76; 252/645
[58] Field of Search .............. 424/1.1; 252/645; 73/73, 76; 250/303; 436/56

[56] References Cited

U.S. PATENT DOCUMENTS 2,575,169  11/1951  Green, Jr. ........................ 73/73
4,014,433  3/1977  Cerwin ............................ 206/63.3

OTHER PUBLICATIONS

Chenion et al., "Study of Adsorption and Desorption of Steam by Materials", B. Soc. Chim, France, (12) 1973, pp. 3273–3277 and English Translation.

Primary Examiner—John S. Maples
Attorney, Agent, or Firm—Anthony M. Santini

[57] ABSTRACT

A radioactive assay method for measuring the humectant properties of cosmetic or non-cosmetic formulations or substances of any consistency, e.g. biological or synthetic liquids, solids, solutions, suspensions, isolated stratum coreum and hair, by measuring the uptake of radioactive water vapor.

15 Claims, 9 Drawing Sheets

//  4,965,450

RADIOACTIVE ASSAY FOR MEASURING WATER ABSORPTION BY HUMECTANTS

This application is a continuation-in-part application of U.S. Ser. No. 815,484, filed Jan. 2, 1986, now abandoned.

This present invention relates to a sensitive, rapid and accurate radioactive assay method to quantitate the water absorbing (ie. humectant) properties of materials, mixtures of materials and complex substances.

BRIEF DESCRIPTION OF THE INVENTION

Methods for isolating and purifying humectant macromolecules are described, and they have been characterized in terms of their molecular weights and amino acid and lipid compositions. Proteolipids absorbed up to 120 times their weight with water, and their moisturizing properties on human skin following topical application were demonstrated using electrical impedance measurements. Immuno-fluorescence and skin layering studies demonstrated that the proteolipids are present in skin in the epidermal stratum granulosum and stratum corneum.

It is generally accepted that the main factor responsible for dry skin is the lowered moisture content of the stratum corneum. A major objective of moisturizing creams and lotions, therefore, is to increase the water content of this structure either by preventing evaporation by occlusion or by addition of the emulsion of humectant substances which bind water. We have discovered an in vitro radioactive assay to quantitate water absorption by humectant molecules. The assay is based on the uptake of $^3$H-water vapor by the dehydrated humectant substance in a closed chamber. The assay has been standardized using urea, sodium pyrrolidone carboxylic acid (NaPCA), glycerol, hyaluronic acid and native collagen and water uptake was examined in terms of weight of humectant, temperature (5°, 24°, 32°, 50° C., relative humidity (RH) (10, 40, 100%) and time to equilibration (8–96 hours). As seen with other assay systems, maximal water binding was highly dependent on RH; temperature increased the rates of water binding but had little effect on the amount bound. At 100% RH, NaPCA was the best humectant, followed by urea > glycerol > hyaluronic acid > native collagen.

Our results as to maximal absorption of water by the substances tested compare with published values obtained using conventional gravimetric measurement techniques. The advantages of the assay are its sensitivity, accuracy, reproducibility and speed at which large numbers of samples can be assayed.

BACKGROUND OF THE INVENTION

The stratum corneum from animal skin arises as a result of a programmed differentiation of underlying epidermal keratinocytes. The terminal events involved in the formation of this non-living structure from living stratum granulosum cells are complex and the molecular mechanisms are incompletely understood. The process involves nuclear expulsion, externalization of lipid-containing lamellar bodies, enzyme-catalyzed degradation and selective loss of all major classes of macromolecules and cellular dehydration. The dehydrated cells become flattened and they adhere tightly to form the final laminated structure which provides a selective barrier to the entry or exit of substances to or from the skin.

Numerous lines of investigation have led to the principle that the extent of hydration of the stratum corneum is responsible for the clinical feel and appearance of dry skin. The stratum corneum from normal skin contains 10–20% water, whereas the stratum corneum from clinically dry skin contains 5–10% water. Dry stratum corneum can be treated by direct addition of water, by occlusion to prevent water evaporation or by addition of substances with humectant (i.e. water-retaining) activity. Humectants commonly used in skin moisturizing products include glycerol, urea, propylene glycol, mineral oil and pyrollidine carboxyllic acid. More recently, naturally-occurring macromolecules such as collagen, hyaluronic acid, elastin or placental proteins have been used as humectants. Although all these substances are reasonably good humectants, it is clear that none of them are involved in the natural mechanisms of stratum corneum moisturization.

Since first proposed in 1952 that the clinical feel and appearance of dry skin directly results from a lack of water in the stratum corneum, the skin care cosmetic industry has formulated creams and lotions designed to hydrate the structure. This is accomplished by addition of water to the formula, inclusion of film-forming occlusive oils and waxes which cause water accumulation by slowing its exit from the skin, or by addition of hygroscopic humectant substances which hold water to the surface. Numerous investigators have employed gravimetric techniques to measure the water-binding capacity of humectant substances, either alone or on isolated stratum corneum. Generally, the substance is equilibrated at 0% relative humidity (RH) to obtain the dry weight and then after re-equilibration at a given RH and temperature for 20 to 40 days, the substance is again weighed. This approach yields accurate information, but it is extremely time-consuming and requires large amounts of assay materials.

We have now discovered an extremely rapid and sensitive method to measure the water-binding capacity of substances. The method is an in vitro radioactive assay system. Assay results can be obtained within a 20-hour time period using microgram quantities of materials and the procedure can assess humectant properties of single ingredients, finished formulas, complex mixtures or biological structures such as while skin, stratum corneum or hair. Using standard humectant substances, our assay results for maximal water binding agree with published results which use the conventional time consuming and laborious gravimetric techniques described above.

BRIEF DESCRIPTION OF THE DRAWING

The invention may be better understood by reference to the figures in which.

Figure 5:
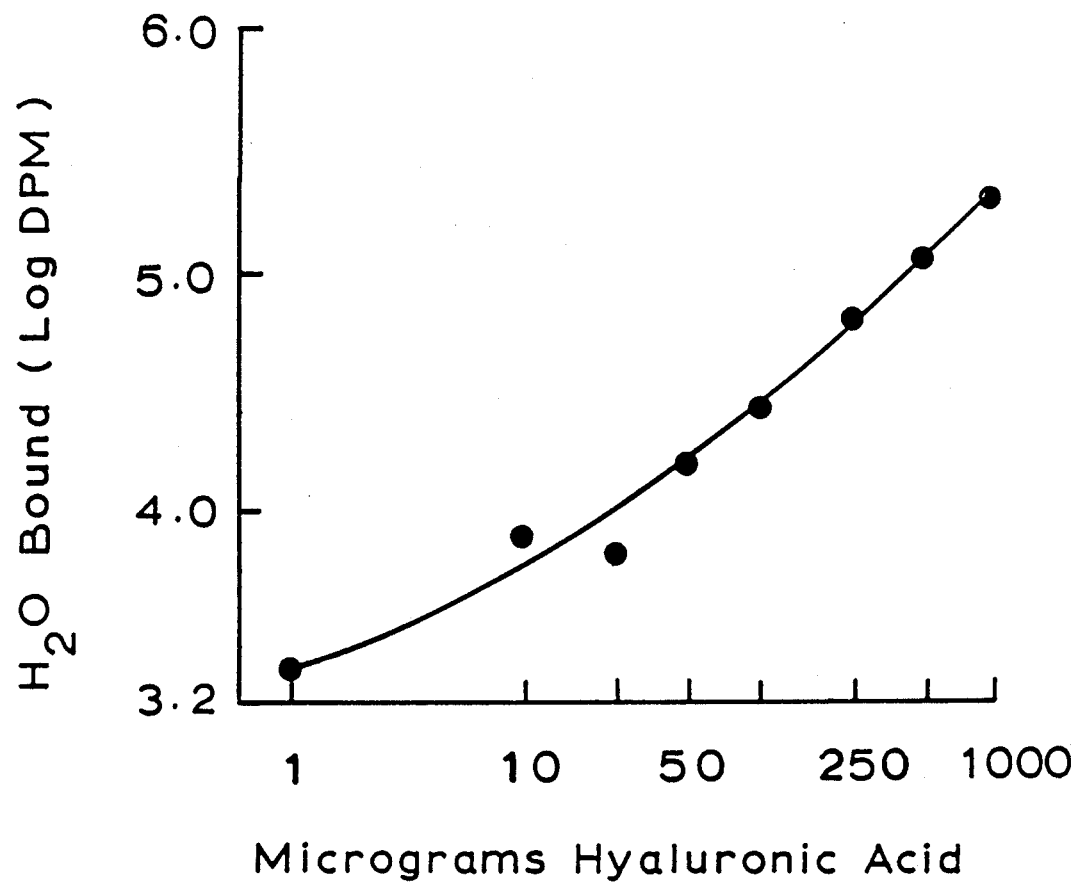
Figure 6:
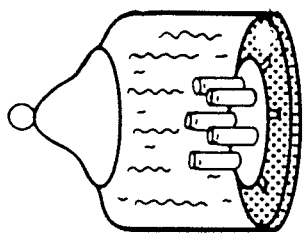
Figure 6:
Figure 6:
Figure 6:
Figure 6:

The data for the Figure represents the average values of all the temperature from FIGS. 1, 2, 3 at the given relative humidity;

FIG. 5 illustrates the uptake of $^3$H-water by various quantities of hyaluronic acid, measured at 100% relative humidity, 24° C.; and FIG. 6 illustrates a preferred embodiment of the radioactive assay method of the present invention.

DESCRIPTION OF THE INVENTION

The following will outline in detail the methods we have used to isolate, purify and characterize a unique group of humectant proteolipid molecules from hairless mouse or human epidermis, cultured human skin epidermal cells and bovine snout epidermis. Their chemical characterization, tissue localization, humectant properties and moisturizing effects on human skin will be described.

The epidermis is first separated from the dermis. The epidermis is then submitted to a series of treatments to separate proteins, polysaccharides, nucleic acids, free polar lipids and free fatty acids to obtain pure proteolipid compounds. These proteolipid compounds are fat soluble and are then treated to convert them to water soluble compounds.

We have also discovered a useful assay method to quantitate the water-absorbing properties of humectant substances. The assay is extremely sensitive, fast, accurate and reproducible and the results compared with published values obtained using conventional gravimetric techniques. The method is simple to perform. To prevent contamination, appropriate caution should be exercised to ensure that the individual performing it does not inhale or otherwise contact the $^3$H-water vapor, the chamber joints should be well sealed with vacuum grease and wrapped and sealed in water-tight plastic bags during the incubation, and all manipulations of open chambers and vials in a chemical fume hood with a minimum negative air flow preferably of 150 linear feet/minute.

We used known humectant substance to standardize the assay. Urea and NaPCA are constituents of the "natural moisturizing factor" (NMF) from skin, which is believed to be responsible for the water-binding capacity of the stratum corneum. Glycerol is extremely hygroscopic and absorbs water until equilibrium with the ambient RH is attained. The protein collagen and the glycosaminoglycan hyaluronic acid are macromolecular constituents of the dermis which in recent years have been formulated into topical skincare products to enhance moisturization efficacy. Although the method was developed using known humectants dissolved in water, it is also useful to assess humectancy of complex oil-in-water or water-in-oil emulsions. As with the single solutes, measured amounts of the emulsion are first dehydrated by, for example, vacuum drying, spray drying, simple heating, lyophylization or any appropriate drying chamber, and then placed into the humectant water chambers.

The processes are defined in detail in the following specific examples:

EXAMPLES 1 TO 3

Proteolipid Extraction and Purification. From Mouse, Human and Bovine Tissue.

To isolate epidermis from hairless mice or human cadavers, full thickness skin pieces were placed dermis down onto plastic petri dishes, which were floated on a 60° C. water bath for one minute. The epidermis was then removed by scraping with a scalpel. Epidermis from bovine snout was dissected from freshly slaughtered or frozen tissues. After washing with cold phosphate-buffered saline, the tissues were suspended in 5 volumes of ice-cold chloroform:methanol (1:1), and 0.01 volumes of 2M KCl was added. The tissue was homogenized on ice for 30 seconds and stirred at room temperature for 30 minutes. The homogenate was filtered through defatted Whatman #1 paper. The filtrate was centrifuged and the upper chloroform phase collected and concentrated to one-half the initial tissue volume by rotary evaporation. Five volumes of cold acetone were added and the solution was allowed to remain at −20° C. for 2 hours. After Centrifugation in a refrigerated centrifuge, the precipitate was washed 3 times with 10 volumes of cold ethanol:ether (1:1). The pellet was suspended in one-half the original tissue volume of chloroform:methanol:HCl (15:15:0.1) and precipitated by the addition of 5 times the volume of acetone at −20° C. overnight. The precipitate was collected by centrifugation and suspended in one-half the original tissue volume of chloroform:methanol (1:1). In order to transfer the proteolipids to the water phase, the solution was placed at 37° C. and nitrogen was bubbled into the solution as water was slowly added in a dropwise fashion until cloudiness developed. Nitrogen bubbling was continued until the chloroform and methanol evaporated, at which time the solution clarified.

EXAMPLE 4

Proteolipid Amino Acid and Lipid Content.

The amino acid composition of the proteolipid fraction from cultured human epidermal cells is shown in Table I. Approximately half the residues are hydrophobic, and would be expected to insert into the lipid portion of the cell membrane. The remaining half are hydrophilic, and could bind water.

The lipid portion of the human proteolipid fraction was removed by treating the material overnight by acid methanolysis (5% HCL in methanol at 70° C.). The fatty acid methyl esters were then identified by gas chromatography (Table II). Unidentified components accounted for approximately 7% of the total lipids, which were not included in the calculations.

TABLE I

| HUMAN EPIDERMAL PROTEOLIPID | |
|---|---|
| AMINO ACID | RESIDUES/1000 |
| HYDROPHOBIC | |
| Alanine | 91 |
| Leucine | 127 |
| Isoleucine | 54 |
| Valine | 56 |
| Proline | 56 |
| Phenylalanine | 62 |
| Tryptophane | 21 |
| Methrinine | 31 |
| Total | 496 |
| MILDLY HYDROPHILIC | |
| Serine | 69 |
| Threonine | 61 |
| Tyrosine | 44 |
| Asparagine | N.D. |
| Glutamine | N.D. |
| Cysteine | 23 |
| Glycine | 87 |
| Total | 284 |
| VERY HYDROPHILIC | |
| Lysine | 36 |

TABLE I-continued

| HUMAN EPIDERMAL PROTEOLIPID | |
|---|---|
| AMINO ACID | RESIDUES/1000 |
| Arginine | 36 |
| Histidine | 18 |
| Aspartic Acid | 63 |
| Glutamic Acid | 65 |
| Total | 218 |

TABLE II

| LIPID CONTENT OF HUMAN PROTEOLIPID FRACTION | |
|---|---|
| LIPID | % Of Total Lioid Wt. |
| C-16:0 | 37.0 |
| C-18:0 | 25.8 |
| C-18:1 | 15.3 |
| C-20:3 | 14.0 |
| Unidentified | 7.0 |

EXAMPLE 5

Proteolipid Localization in the Epidermis.

The localization of proteolipids in human epidermis was determined using techniques of immuno-fluorescence and skin layering. The 20,000 molecular weight proteolipid species from cultured human epidermal cells was cut from slab SDS-PAGE gels, emulsified with Fruend's complete adjutant and injected into rabbits and sheep. After appropriate times, the immune sera were collected and the indirect immuno-fluorescence stain technique was employed to localize the antigen in frozen sections of human skin. The 20,000 mol. wt. proteolipid localized primarily to the stratum granulosum and stratum corneum. When hairless mouse skin was separated into different layers by trypsinization and examined by extraction, purification and weighing, it was determined that 63% of the total proteolipid was recovered in the stratum corneum, 29% in the stratum granulosum and 8% in the stratum basale (Table III).

TABLE III

PROTEOLIPID CONTENT OF VARIOUS LAYERS OF EPIDERMIS
(From The Hairless Mouse)

| Epidermal Layer | Wet Weight Tissue (g) | Proteolipid Recovered (mg) | % of Wet Wt. | % of Total Proteolioid |
|---|---|---|---|---|
| Stratum corneum | 6.15 | 1.5 | 0.024 | 62.5 |
| Stratum granulosum | 1.14 | 0.7 | 0.061 | 29.2 |
| Stratum basale | 1.50 | 0.2 | 0.013 | 8.3 |

EXAMPLE 6

Humectantcy of Proteolipids

As depicted in FIG. 6, a sensitive radioactive assay procedure was developed to assess the water-absorbing (i.e. humectant) properties of proteolipids and other molecules. A solution or fine suspension of known amounts of the material to be assayed was placed in a scintillation vial and evaporated to dryness in a vacuum centrifuge at 45° C. to remove substantially all water. The vials were then transferred onto a porcelain stand in a glass chamber containing $^3$H-H20 (100 MCi/ml). The chamber was sealed and placed at 37° C. such that the relative humidity quickly equilibrated to 100% to form an atmosphere of radioactive vapor. After 20 hours of radioactive water vapor absorption, the vials were removed from said sealed chamber, scintillatic on fluid was added, and the radioactivity determined in a liquid scintillation counter. For determination of bound water, the amounts of proteolipids or other test substances were varied from 1–50 ug/vial (all in 1 ml solvent), samples and solvent controls were run in triplicate and the water bound/ueg substance was calculated from the slope of the linear DPM/ug substance curve. The results (Table IV) are expressed as ug water bound/ug substance. For comparison, the values for other lipids, hyaluronic acid (a known humectant) and collagen are included. The proteolipids are clearly better humectants than free fatty acids, complex lipids (cerebrosides and ceramides), neutral lipids, hyaluronic acid or collagen.

TABLE IV

| HUMECTANTCY OF VARIOUS SUBSTANCES | |
|---|---|
| SUBSTANCE | ug $H_2O$ Absorbed/ug Substance |
| Epiderman Proteolipids | |
| Murine | 119.8 |
| Bovine | 68.0 |
| Hyaluronic Acid | 19.7 |
| Collagen (Human, Native) | 2.0 |
| Lipids | |
| Neutral lipid mix (Cholesterol, triglycerides, sterol esters, free fatty acids) | 31.7 |
| Palmitic Acid | 9.9 |
| Stearic Acid | 3.3 |
| Cerebrosides | 0 |
| Ceramides | 0 |

EXAMPLE 7

HUMECTANCY ASSAY

Samples to be tested for humectancy were dissolved in high purity distilled water. Water with a measured resistance of 18 megaohms was used. Native bovine collagen was obtained from Pentapharm (lot #3186/150), hyaluronic acid from Sigma (H-1504), the sodium salt of 2-pyrrolidone-5-carboxylic acid from Ajimoto Company, urea from Sigma Chemical Co. (#U=1250) and glycerol from J.T. Baker Chemical Co. (#2136-1). The collagen (mol. wt. approx. 288,000) was first dialyzed against 0.5M acetic acid to remove possible low molecular weight substances such as peptides and salts. The compounds were dissolved in water at concentrations of 1 mg/ml. Water insoluble compounds or substances should be suspended in water or dissolved in any appropriate solvent which can be removed by lyophylization.

One-ml samples of the solutions to be tested from humectancy were pipeted into the bottom of 7 ml glass scintillation minivials. The vials were frozen in an upright position in a dry ice/acetone bath and lyophylized (i.e. freeze-dried) overnight. Control vials contained 1 ml water. This relationship between volumes of humectant and vials was maintained to eliminate possible surface area affects. The dried samples were then placed into a porcelain rack of a sealed drying chamber which contained 100 ml of 50 uCi/ml $^3$H-water (New England Nuclear, NET-001C). The chamber may alternatively be constructed of metal, glass or plastic. $^3$H-water of other specific activity levels may also be used.

The chambers had been pre-equilibrated at 10, 40 or 100% relative humidity, each at 5, 24, 32 or 50° C.

Humidity may be controlled by placing solutes, such as salts, into the radioactive water. Triplicate samples were removed at 8, 24, 48, 72 and 96 hours. To collect the samples, the humidity chambers were removed from the constant temperature incubators and opened in a fume hood with an air flow of 150 linear feet/minute. Other usable temperature regulating devices include a water jacket or electrical mantel affixed to the chamber. Non-bound water vapor which may have collected on the inside of the vials was flashed off by allowing them to stand open exactly 15 minutes in the hood. Six ml of water miscible liquid scintillation counting fluid (Beckman Ready-Solv MP scintillation cocktail) was added to the vials, which were then tightly capped. The radioactivity was determined in a Beckman LS 9800 liquid scintillation counter. Alternative methods for measuring radioactivity include the use of a planchet, windowless counter or Geiger counter. Constant 10% RH was achieved using saturated Lithium Chloride in the $^3$H-water, 40% RH using Magnesium Nitrate in the $^3$H-water and the 100% RH using only $^3$H-water. RH was monitored using an electronic humidity probe (Vaisala Company, Model #HM131).

Figure 1A:
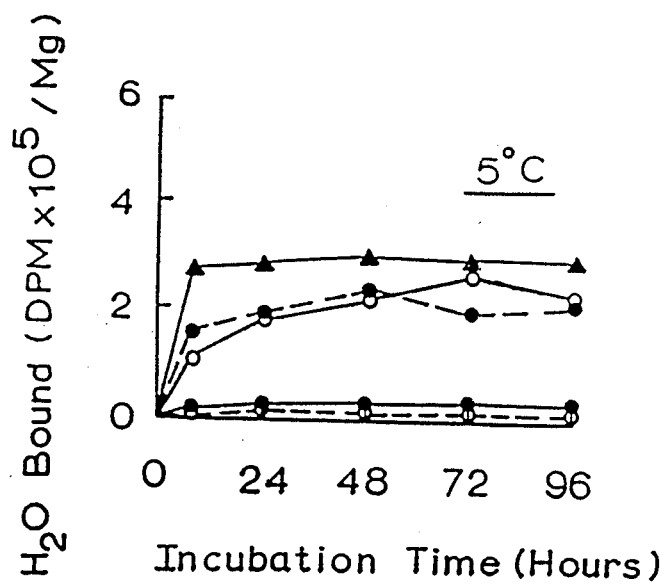
FIGS. 1a–1b illustrate the uptake of $^3$H-water by humectant substances at 10% relative humidity. The temperatures of incubation and the identity of the humectants are indicated on the Figure.
Figure 1B:
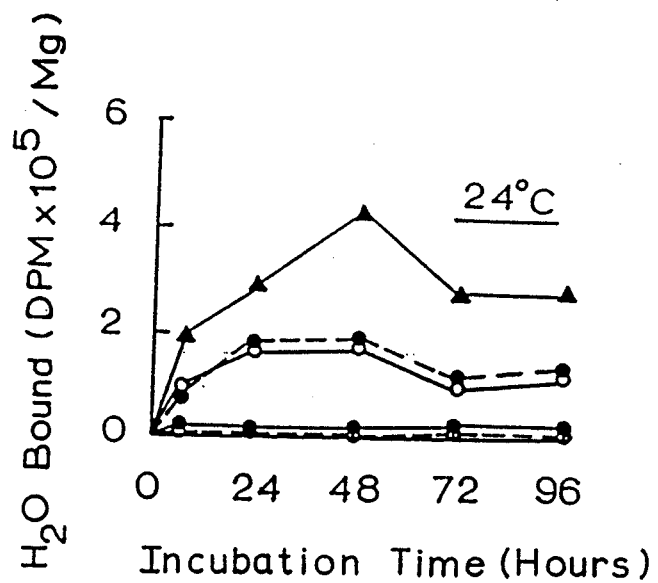
Figure 1C:
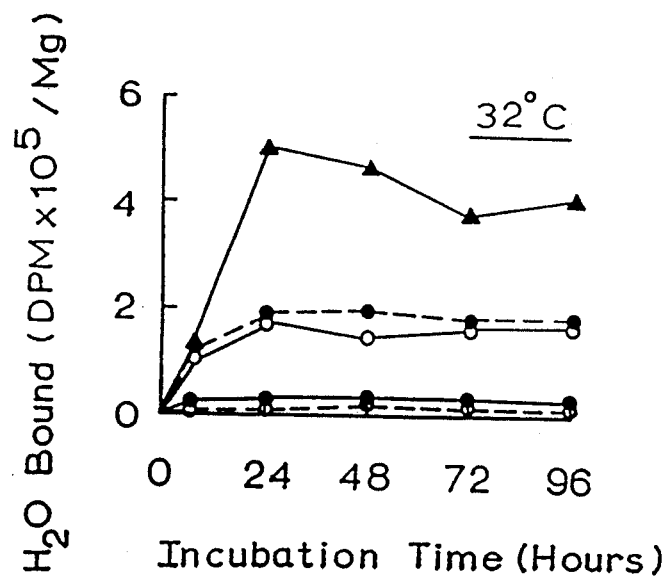
Figure 1D:
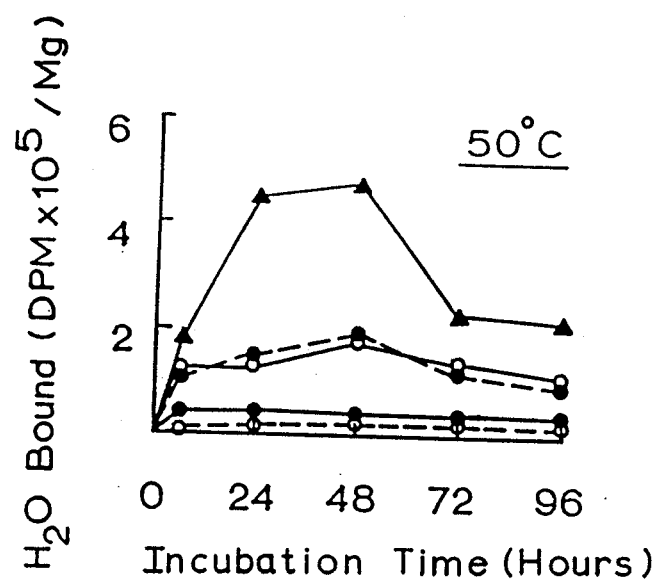
Figure 2A:
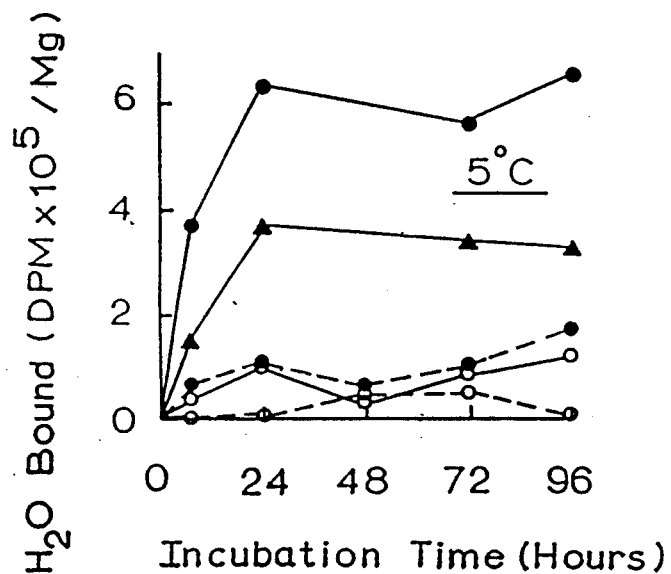
FIGS. 2a–2b illustrate the uptake of $^3$H-water by humectant substances at 40% relative humidity. The temperature of incubation and the identity of the humectants are indicated on the Figure.
Figure 2B:
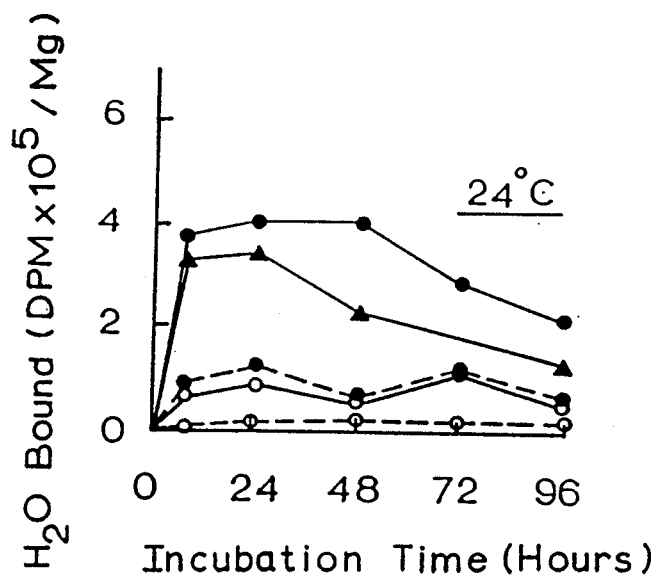
Figure 2C:
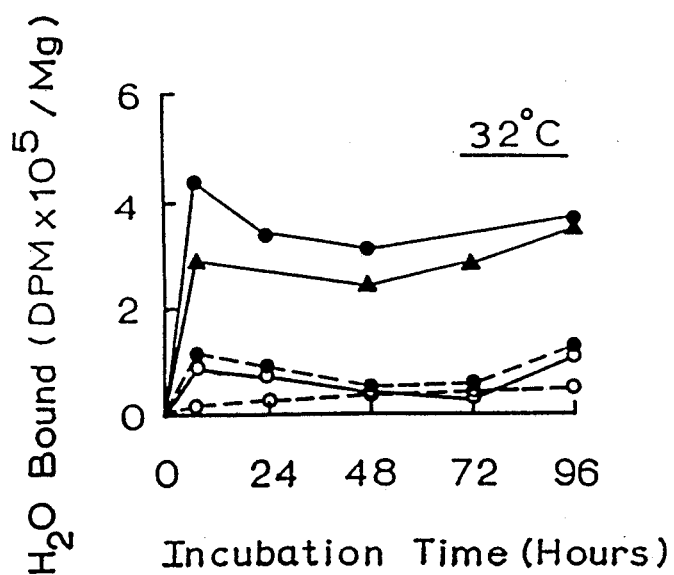
Figure 2D:
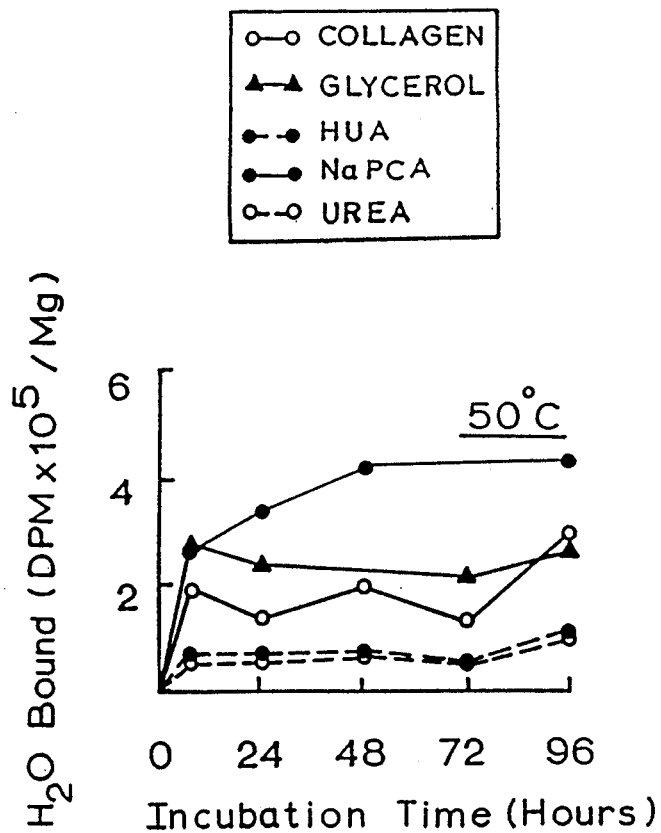
Figure 3A:
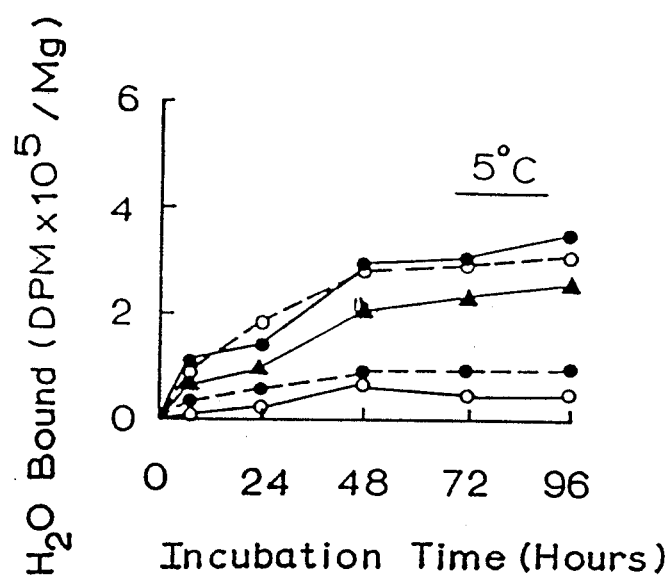
FIGS. 3a–3b illustrate the uptake of $^3$H-water by humectant substances at 100% relative humidity. The temperatures of incubation and the identity of the humectants are indicated on the Figure.
Figure 3B:
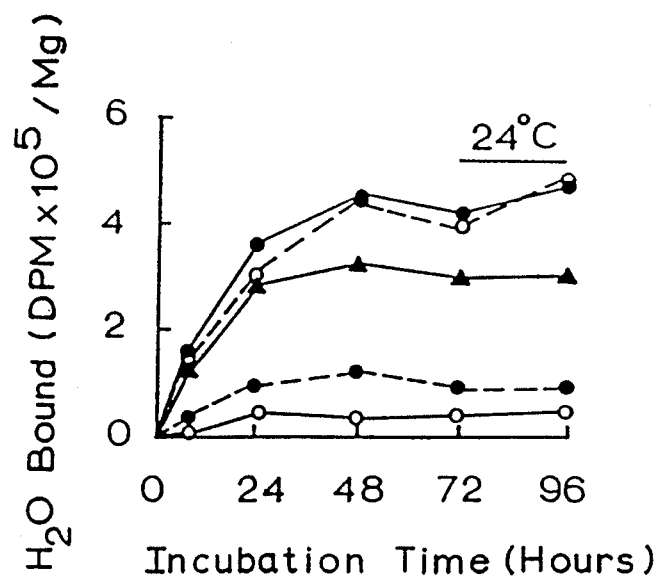
Figure 3C:
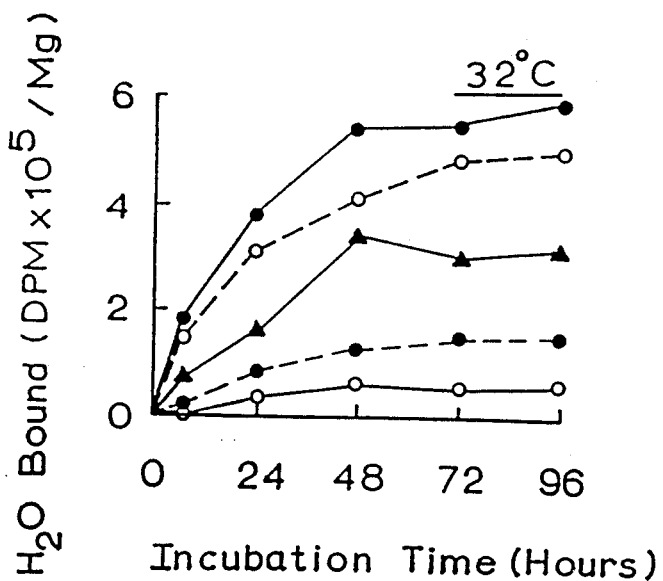
Figure 3D:
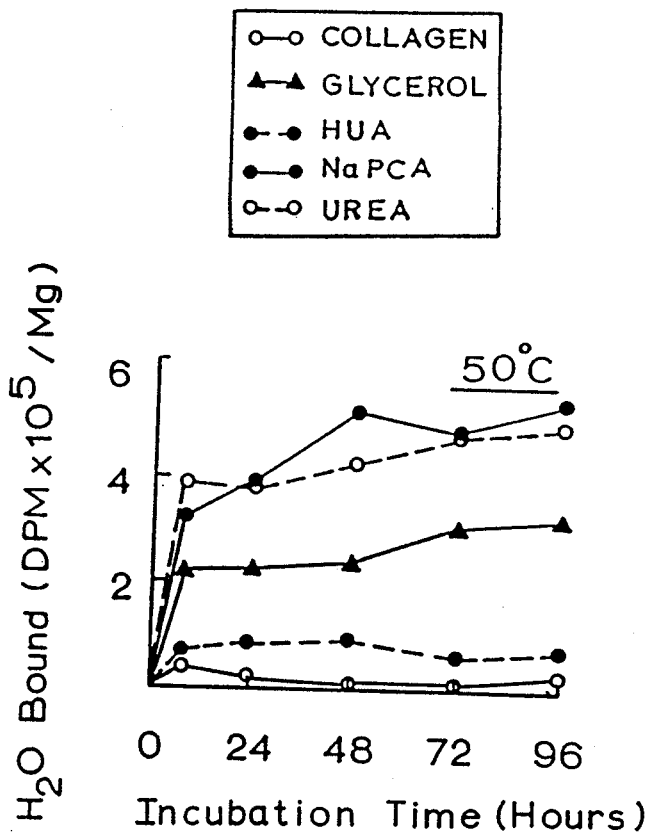
Figure 4:
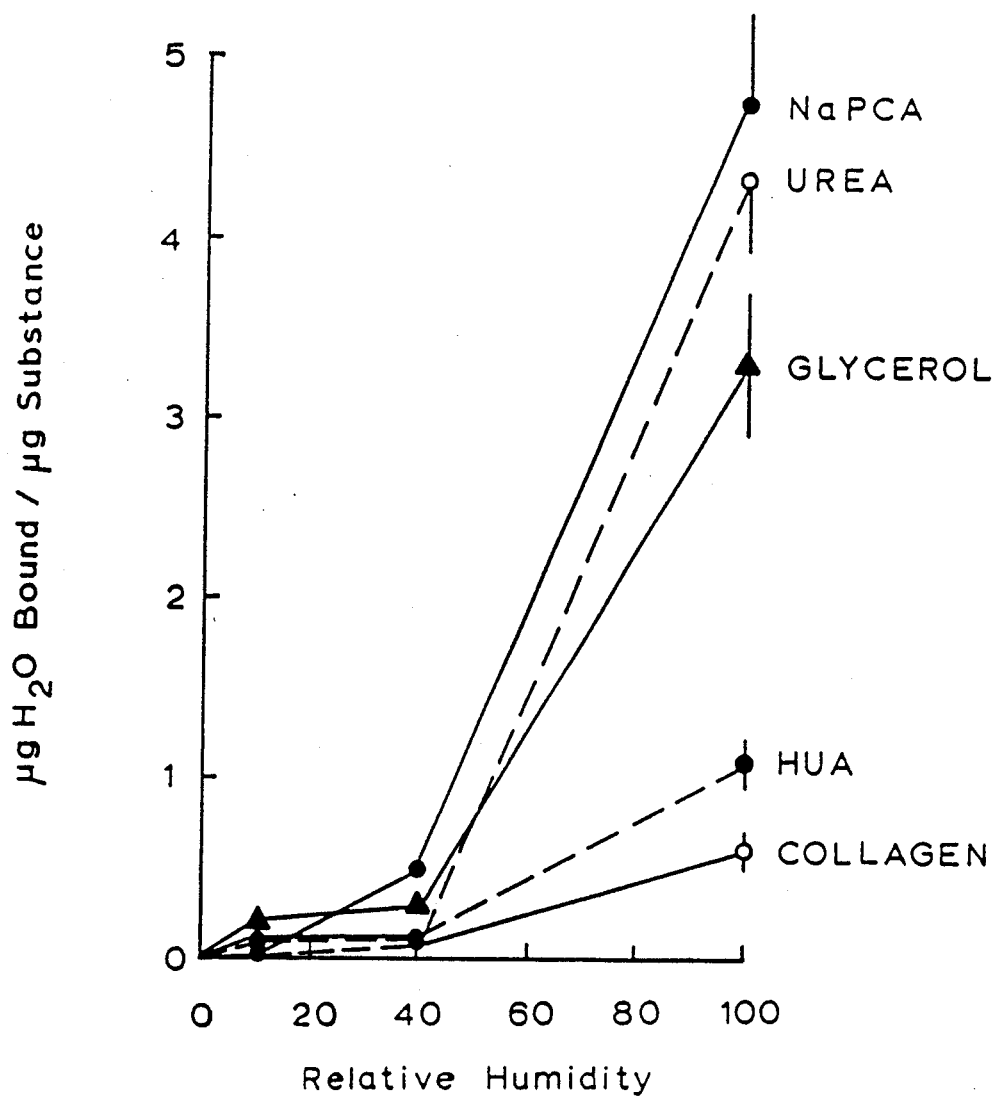
FIG. 4 illustrates the uptake of $^3$H-water by humectant substances at different values of relative humidity.

The water uptake (humectancy) data for several known humectant substances are presented in FIGS. 1, 2 and 3, which represent the water absorbed respectively at 10, 40 and 100% RH. At each humidity and temperature tested, absorption was linear with time until equilibration generally occurred. For all the compounds tested, the time to equilibration was inversely related to the temperature. At 5° C., 2 to 3 days were required for complete saturation whereas at 50° C. equilibration occurred as early as 8 hours. Maximal absorption was relatively independent of temperature, but saturation values increased dramatically with increasing RH. The effects of RH on absorption is presented in Table V For all the substances, relatively little water binding occurred at 10 or 40% RH, compared to that seen at 100% RH. Under these optimal binding conditions, NaPCA bound about 4.7X, urea 4.3X, glycerol 3.3X, hyaluronic acid 1.1X and collagen 0.6X their weights with water. FIG. 4 represents the water absorbed at the average value of all the temperatures from FIGS. 1, 2 and 3 at the given relative humidity.

The maximal binding of water was linear with quantity of humectant material over a wide range, although it has been our experience that minimal threshold quantities are preferable. Substances in amounts less than 10 micrograms may not yield reproducible results. As an example, the water binding capacity for a commercially-available sample of hyaluronic acid is shown in FIG. 5. Water uptake was linear at all values between 10 and 1,000 micrograms of material.

For the humectants tested in the assay system of the present invention, maximal water-binding was observed at 100% RH, whereas at low (10% RH) and intermediate (40% RH) values of RH, little change in equilibrium value water binding occurred (see Table V). Our results also showed that as the temperature increased, the rates of equilibration of the humectant with the water increased, but the amounts bound at saturation were relatively independent of temperature. These results are in agreement with those reported in the prior art for humectants or isolated stratum corneum. Thus, 100% RH can be used to assess the maximal capacity for a humectant substance or preparation to bind water. However, because little need exists to use a skin humectant under these extreme humid conditions, more practical information can be gained if the substance is tested at lower RH.

TABLE V

Effect of Relative Humidity on Equilibrium Moisture Absorption

| Material | % Water Absorbed[a,b] | | |
|---|---|---|---|
| | 10% RH | 40% RH | 100% RH |
| Hyaluronic acid | 9 ± 2 | 12 ± 2 | 108 ± 26 |
| Collagen | 8 ± 1 | 11 ± 1 | 59 ± 25 |
| NaPCA | 1.5 ± 0.4 | 48 ± 13 | 474 ± 105 |
| Urea | 0.7 ± 0.2 | 4 ± 2 | 433 ± 83 |
| Glycerol | 20 ± 3 | 29 ± 6 | 330 ± 79 |

[a] $\frac{\text{ug water absorbed}}{\text{ug dry material}} \times 100$

[b] Each data point represents three separate determinations averaged over the four temperatures.

This invention should be understood to cover any modifications of the methods described for measuring moisture-binding capacities of simple substances or complex mixtures of substances. For example, variations in the vials used to hold samples, method of drying samples, all temperatures at which the assay is conducted, the amounts and specific activities of the radioactive water which is used in the chamber, the RH under which the assay is performed, the design of the humectant chamber and the kinetics and concentrations of samples tested. The invention should also be understood to cover the testing of the individual ingredients, or finished formulations for water absorbing capacities and to use on complex structures such as whole skin, stratum corneum or hair.

What is claimed is:

1. A method for determining the humectancy of an epidermal moisturizing material comprising (1) drying said material to remove substantially all water; (2) placing said material in a sealed chamber in the presence of radioactive water and allowing said material to remain in said sealed chamber for a pre-determined period of time to absorb radioactive water vapor; and (3) removing said material from said sealed chamber and measuring the radioactivity of said material.

2. The method of claim 1 wherein said measurement is taken using a liquid scintillation counter, planchet, windowless counter or Geiger counter.

3. The method of claim 1 wherein said sealed chamber is made of glass, metal, plastic or ceramic.

4. The method of claim 1 wherein said material can form a cosmetic formulation or substance.

5. The method of claim 4 wherein said material can be biological or synthetic liquids, solids, solutions or suspensions.

6. The method of claim 1 wherein said material is dried under vacuum, by lyophylization, spray drying, heating or in a drying chamber.

7. The method of claim 6 wherein said material is dried under vacuum at about 45° C.

8. The method of claim 6 wherein said drying takes place in a scintillation vial.

9. The method of claim 1 wherein said radioactive water vapor is formed by applying a temperature to said chamber whereby the humidity in said chamber rapidly reaches 100%.

10. The method of claim 9 wherein said sealed chamber is submitted to a temperature of about 37° C.

11. The method of claim 9 wherein said material is allowed to remain in said sealed chamber for about 20 hours.

12. The method of claim 9 wherein said temperature is controlled by placing said chamber into a temperature-controlled incubator or by affixing a temperature-regulating device thereto.

13. The method of claim 12 wherein said temperature-regulating device is a water jacket or electrical mantel.

14. The method of claim 9 wherein said humidity is controlled by placing solutes into said radioactive water.

15. The method of claim 14 wherein said solutes are salts.

* * * * *